United States Patent [19]

Browder et al.

[11] Patent Number: 4,939,297
[45] Date of Patent: Jul. 3, 1990

[54] EXTRACTION PROCESS FOR REMOVAL OF IMPURITIES FROM TEREPHTHALIC ACID FILTRATE

[75] Inventors: Larry W. Browder; James C. Medlin; Art T. Spaugh, Jr., all of Kingsport, Tenn.

[73] Assignee: Eastman Kodak Company, Rochester, N.Y.

[21] Appl. No.: 361,176

[22] Filed: Jun. 5, 1989

[51] Int. Cl.$^5$ .............................................. C07C 51/43
[52] U.S. Cl. .................................... 562/485; 562/414
[58] Field of Search ................................ 562/485, 414

[56] References Cited

U.S. PATENT DOCUMENTS

| 3,673,154 | 6/1972 | Trevillyan | 562/414 |
| 4,340,752 | 7/1982 | List et al. | 562/485 |
| 4,356,319 | 10/1982 | Roffia et al. | 562/414 |

Primary Examiner—Werren B. Lone
Assistant Examiner—Vera C. Clarke
Attorney, Agent, or Firm—Charles R. Martin; William P. Heath, Jr.

[57] ABSTRACT

A method for removing impurities from an oxidative terephthalic acid synthesis mother liquor containing acetic acid, water, corrosion metals, a metal catalyst and organic impurities, comprising the steps of (a) removing from the mother liquor by evaporation from 50-95% of the acetic acid and water contained therein; (b) adding an amount of water to the concentrated mother liquor sufficient to dissolve the metal catalyst and form an aqueous mixture; (c) extracting the aqueous mixture by counter-current extraction with a substantially water-insoluble organic solvent, to produce a lighter phase containing the organic solvent, a minor amount of the water, acetic acid and the organic impurities and a heavier phase containing a major amount of the water, corrosion metals and the metal catalyst, and; (d) removing the corrosion metals from the heavier phase by heating and filtering, and; (e) removing the organic impurities from the lighter phase by distillation.

15 Claims, 1 Drawing Sheet

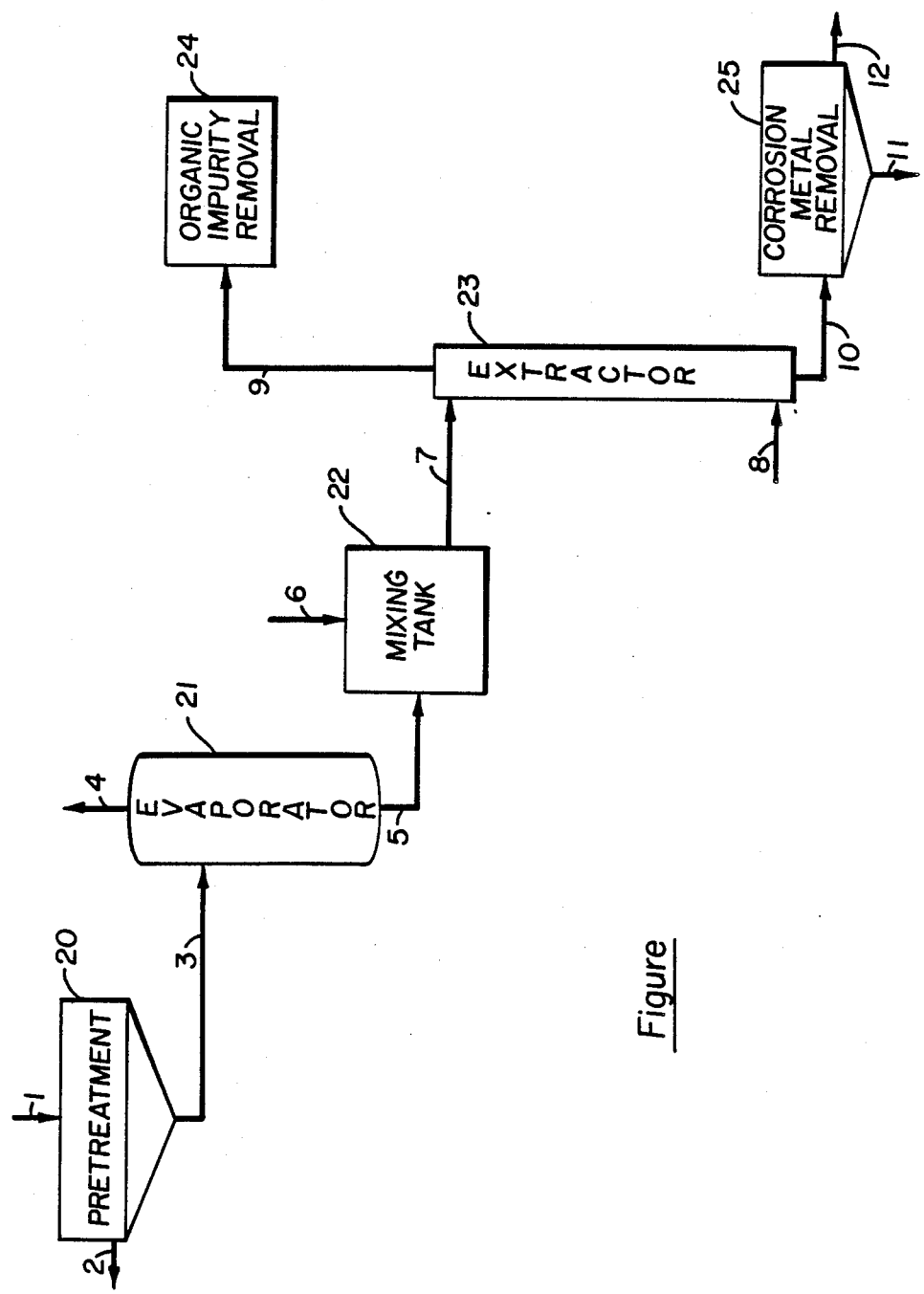
Figure

EXTRACTION PROCESS FOR REMOVAL OF IMPURITIES FROM TEREPHTHALIC ACID FILTRATE

The invention relates to the removal of impurities and the recovery of a heavy metal catalyst from a mother liquor produced in the synthesis of terephthalic acid. More particularly, the process involves the addition of water to a concentrated mother liquor to solubilize the heavy metal catalyst and then subjecting the aqueous mixture so formed to a counter-current extraction to remove organic impurities.

Terephthalic acid (TPA) is an intermediate in the production of polyesters for plastics and fiber applications. Commercial processes for the manufacture of TPA are based on the heavy-metal catalyzed oxidation of p-xylene, generally with a bromide promoter in acetic acid solvent. Due to the limited solubility of TPA in acetic acid under practical oxidation conditions, a slurry of TPA crystals is formed in the oxidation reactor. Typically, the TPA crystals are withdrawn from the reactor and separated from the reaction mother liquor using conventional solid-liquid separation techniques. The mother liquor, which contains most of the catalyst and promoter used in the process, is recycled to the oxidation reactor. Aside from the catalyst and promoter, the mother liquor filtrate also contains dissolved TPA and many by-products and impurities. These by-products and impurities arise partially from minor impurities present in the p-xylene feed stream. Other impurities arise due to the incomplete oxidation of p-xylene resulting in partially oxidized products. Still other by-products result from competing side reactions in the oxidation of p-xylene to terephthalic acid.

The solid TPA crystals obtained by solid-liquid separation are generally washed with fresh solvent to displace the major portion of the mother liquor and then dried to remove most of the acetic acid solvent. The dried, crude TPA crystals are contaminated with impurities which were present in the mother liquor since these impurities are coprecipitated with the TPA crystals. Impurities are also present due to occlusion in the TPA crystal structure and due to incomplete removal of the mother liquor by the fresh solvent wash.

Many of the impurities in the mother liquor recycle are relatively inert to further oxidation. Such impurities include isophthalic acid, phthalic acid and trimellitic acid for example. Impurities which undergo further oxidation are also present, such as for example 4-carboxybenzaldehyde, p-toluic acid and p-tolualdehyde. The concentration of oxidation inert impurities tends to accumulate in the mother liquor stream. The concentration of these inert impurities will increase in the mother liquor until an equilibrium is reached whereby the amount of each impurity contained in the dry TPA product balances its rate of formation or addition to the oxidation process. The normal level of impurities in crude TPA makes it unsuitable for direct use in most polymer applications.

Traditionally, crude TPA has been purified either by conversion to the corresponding dimethyl ester or by dissolution in water with subsequent hydrogenation over standard hydrogenation catalysts. More recently, secondary oxidative treatments have been used to produce polymer-grade TPA. Irrespective of the method used to purify TPA to render it suitable for use in polyester manufacture, it is desirable to minimize the concentrations of impurities in the oxidation mother liquor and thereby facilitate subsequent purification of TPA. In many cases, it is not possible to produce a purified, polymer-grade TPA unless some means for removing impurities from the recycled mother liquor is utilized.

One technique for impurity removal from a recycle stream commonly used in the chemical processing industry is to draw out or "purge" some portion of the recycle stream. Typically, the purge stream is simply disposed of or, if economically justified, subjected to various treatments to remove undesired impurities while recovering valuable components. The amount of purge required for control of impurities is process-dependent; however, a purge amount equal to 10–40% of the total mother liquor filtrate is usually sufficient for TPA manufacture. In the production of TPA, the level of mother liquor purge necessary to maintain acceptable impurity concentrations, coupled with the high economic value of the heavy metal catalyst and solvent components of the mother liquor, make simple disposal of the purge stream economically unattractive. Thus, there is a need for a process which recovers essentially all of the expensive heavy metal catalysts and acetic acid contained in the mother liquor while removing a major portion of the impurities present in the purge stream. The heavy metal catalyst should be recovered in an active form suitable for reuse by recycling to the p-xylene oxidation.

A variety of methods have been proposed for the recovery of solvent and oxidation catalyst after removing the major portion of impurities in the mother liquor purge stream. All of these methods involve the initial step of concentrating the mother liquor stream by evaporating the solvent prior to further treatment. In all cases a major portion, and in many cases essentially all, of the acetic acid and water present in the mother liquor are removed.

U.S. Pat. No. 3,673,154 teaches the adjustment of acidity in the concentrated mother liquor either by control of the amount of solvent distilled or by addition of water, to obtain a solution pH greater than 3.0. This pH adjustment results in the precipitation of insoluble salts of corrosion metals, typically iron and chromium, which may then be removed by filtration. This reference also teaches the separation of organic impurities from the catalyst by precipitation of cobalt carbonate, which is then filtered and reconverted to soluble cobalt acetate by the addition of acetic acid.

A disadvantage of this approach is the need to remove a high fraction of the acetic acid and water present to avoid the addition of large amounts of water in the pH adjustment step. This can lead to problems with fouling of heat exchange surfaces in the evaporator. Another disadvantage is the large quantity of alkali metal carbonate salt required to precipitate the cobalt catalyst and the associated consumption of acetic acid both in neutralizing the catalyst-containing solution and in regenerating the soluble cobalt acetate. Still another disadvantage is the potential difficulty in filtering and washing the cobalt carbonate precipitate.

U.S. Pat. No. 4,356,319 discloses a process in which the catalyst-containing mother liquor is concentrated to a lesser extent than U.S. Pat. No. 3,673,154 by removing 70–90% of the acetic acid and water present. The concentrate, which includes 2–6% water, is rapidly cooled to 25° C. to form a precipitate containing TPA and by-products, plus a substantial portion of the heavy metal catalyst in the original mother liquor. Solids are separated by filtration and all or part are recycled to the oxidation process. The filtrate which contains the remaining heavy metal catalyst is treated with a combination of water and an extraction solvent such as xylene, isobutyl acetate or sec-butyl acetate. The resulting aqueous and organic phases are separated by decantation. The aqueous phase which contains the dissolved catalyst is recycled to the oxidation reactor. The organic phase is distilled to recover acetic acid and the extraction solvent leaving a residue containing the organic impurities. There are several disadvantages to this approach. One disadvantage is that no means is provided for removal of corrosion metals. Another disadvantage is that the precipitate formed by rapid cooling of the concentrated mother liquor contains a substantial amount of the unwanted impurities from the mother liquor which result from coprecipitation, occlusion in the crystal, etc. Further, the precipitate obtained is sticky due to the present of tar-like high boiling compounds which pose difficult solid-liquid separation problems. The overall inefficiency of this approach necessitates a high rate of mother liquor purge to achieve the desired level of impurity removal.

We have invented a method for removing impurities from the mother liquor in which the heavy metal catalyst may be recovered in active form for reuse in the oxidative synthesis. Also in our process a substantial amount of the organic impurities are removed thus reducing the coprecipitation of organic impurities with TPA. The relatively high efficiency of our process for removing organic impurities avoids the need for an excessive purge rate to control impurity concentrations in the mother liquor. Furthermore, our invention provides a convenient and practical means for separating corrosion metals from the recovered heavy metal catalyst. In addition, because the invention does not involve precipitation of the organic impurities or the catalyst, which would require subsequent liquid-solids separations equipment, mechanical difficulties and exposure of personnel to process chemicals are avoided.

Our invention can be broadly described as a method for removing impurities from an oxidative terephthalic acid synthesis mother liquor containing acetic acid, water, a metal catalyst and organic impurities, comprising the steps of (a) concentrating the mother liquor by evaporating 50-95% of the acetic acid and water contained therein, (b) adding an amount of water to the concentrated mother liquor sufficient to dissolve the metal catalyst and form an aqueous mixture, (c) extracting the aqueous mixture by counter-current extraction with a substantially water-insoluble organic solvent to produce a lighter phase containing the organic solvent, a minor amount of the water, acetic acid and the organic impurities and a heavier phase containing a major amount of the water, the corrosion metals, and the metal catalyst, and (d) removing the corrosion metals from the heavier phase by heating and filtering, and (e) removing the organic impurities from the lighter phase by distillation.

A more complete understanding of our invention can be obtained by considering the following specific embodiment, including the Figure which illustrates this embodiment. In the Figure there is shown an extractor where there is fed the aqueous mixture prepared by concentrating the mother liquor and then adding water. The lighter phase containing the organic solvent and organic impurities and a heaver phase containing the corrosion metals and the metal catalyst is withdrawn from the extractor.

Although the composition of the various streams in the process varies depending on process conditions, a typical composition of the streams is shown in the below Table. In this Table the components are shown in the left hand column and the amount of these components in each of the streams in the Figure are shown in the numbered column corresponding to the number of the stream in the Figure.

| | Process Material Balance Stream in Figure | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Acetic Acid | 915 | — | 915 | 793 | 122 | — | 122 | — | 121 | 1 | 1 | — |
| Water | 55 | — | 55 | 54.5 | 0.5 | 150 | 150.5 | — | 59.5 | 91 | 91 | — |
| n-Propyl Acetate | — | — | — | — | — | — | — | 900 | 896.3 | 3.7 | 3.7 | — |
| Terephthalic Acid | 0.71 | 0.23 | 0.48 | — | 0.48 | — | 0.48 | — | 0.47 | .01 | .01 | — |
| Isophthalic Acid | 5.83 | 1.60 | 4.23 | — | 4.23 | — | 4.23 | — | 4.01 | .22 | .10 | .12 |
| Phthalic Acid | 3.81 | .01 | 3.80 | .03 | 3.77 | — | 3.77 | — | 3.01 | .76 | .76 | — |
| Benzoic Acid | 8.12 | .04 | 8.08 | .59 | 7.49 | — | 7.49 | — | 7.49 | — | — | — |
| 4-Carboxybenz-aldehyde | 1.56 | .06 | 1.50 | .01 | 1.49 | — | 1.49 | — | 1.48 | .01 | — | .01 |
| Trimellitic Acid | 1.17 | .02 | 1.15 | — | 1.15 | — | 1.15 | — | 0.59 | .46 | .46 | — |
| Paratoluic Acid | 2.96 | .04 | 2.92 | .15 | 2.77 | — | 2.77 | — | 2.77 | — | — | — |
| Paratolualdehyde | 0.51 | — | 0.51 | 0.01 | 0.50 | — | 0.50 | — | 0.50 | — | — | — |
| Others | 2.5 | — | 2.5 | — | 2.5 | — | 2.5 | — | 2.49 | .01 | .01 | — |
| Organic Bromide | 1.30 | — | 1.30 | — | 0.90 | — | 0.41 | — | 0.41 | — | — | — |
| Ionic Bromide | 0.34 | — | 0.34 | — | 0.74 | — | 1.23 | — | — | 1.23 | 1.23 | — |
| Cobolt | 1.44 | — | 1.44 | — | 1.44 | — | 1.44 | — | 0.01 | 1.43 | 1.42 | .01 |
| Manganese | 0.10 | — | — | — | 0.10 | — | 0.10 | — | — | 0.10 | 0.09 | .01 |
| Corrosion Metals | 0.08 | — | 0.08 | — | 0.08 | — | 0.08 | — | — | 0.08 | .02 | .06 |
| Total | 1000 | 2.0 | 998 | 848 | 150 | 150 | 300 | 900 | 1100 | 100 | 99.8 | 0.2 |

The mother liquor withdrawn from the terephthalic acid oxidative synthesis, which is stream 1 in the Figure and serves as the feed stream for the present extraction process, contains terephthalic acid and numerous additional oxidation by-products and side reactants and additionally contains the heavy metal catalyst, organic bromides which are used as promoters in the oxidation reaction and corrosion metals, such as iron and chromium compounds, which inhibit, reduce or entirely destroy the activity of the catalyst. The expense of the typical heavy metal catalyst requires that it be reused and the build-up of corrosion metals necessitates the removal of these components for satisfactory operation and recycle of the catalyst.

In the first step of the present process, the mother liquor is concentrated by conventional atmospheric flash evaporator 21 to produce stream 4 containing most of the water and a major part of the acetic acid from stream 3 and stream 5 containing the remainder of stream 3. The evaporation removes about 50-95 wt % of the volatile acetic acid and water which are present in the mother liquor. For cost effectiveness it is ever more preferable to remove from 80-90 wt % of the volatile acetic acid and water.

It has been found that pretreatment preceding the concentration of the mother liquor is beneficial in reducing the extraction load in the counter-current extraction step by removing portions of isophthalic acid, a major impurity in the mother liquor which has limited solubility in the extraction solvent. The optional pretreatment consists of heating and filtering stream 1 by conventional means 20 to produce stream 2 containing a portion of the isophthalic acid and stream 3 containing the remainder of the isophthalic acid and most of the remaining components from stream 1. The pretreatment is conducted at a temperature from about 20° C. to about 70° C., preferably 45°-55° C. The pretreatment step, while preferred, is not required for carrying out the process of the present invention in its broadest scope. A comparison of the compositions before and after the pretreatment can be seen by examining the difference in streams 1 and 3.

After evaporation, sufficient water is added to conventional mixer 22 by stream 6 to dissolve the metal catalyst present and form an aqueous mixture stream 7. Generally, about 0.5-1.0 parts water per part of concentrated mother liquor are sufficient to dissolve the catalyst, preferably about 1:1 parts by weight. The addition of water not only solubilizes the metal catalyst in the concentrate, but also aids in pumping the resultant slurry to the extractor. It is desirable to keep stream 7 circulating with an external circulation loop. In a preferred embodiment, a small amount of extraction solvent, generally about 1-10% by weight, preferably about 5% by weight is added to the feed stream to enhance slurry handling by reducing adherence of solids to the side of the slurry feed tank. It is desirable, but not necessary, to subject the aqueous slurry, prior to extraction, to a heat treatment at about 60°-95° C., preferably 80°-90° C. for 0.5-4 hours, preferably 1-2 hours. By this treatment, organic bromides are reacted to yield inorganic bromides which are preferentially retained in the aqueous fraction exiting the extractor. The quantity of bromine-containing compounds purged from the system along with the unwanted impurities is thereby minimized. The heat treatment conserves bromides and simplifies disposal of the organic impurities.

Aqueous mixture stream 7, with or without heat treatment to decompose organic bromides, is fed to the top of a conventional counter-current, agitated extractor 23. Simultaneously, organic solvent stream 8 is fed to the bottom of extractor 23. The aqueous mixture and organic solvent are intimately mixed in the counter-current extractor and the acetic acid, organic impurities and organic solvent form a lighter phase, stream 9, containing a minor amount of the water while the metal catalyst and corrosion metals form a heavier phase, stream 10, containing a major amount of the water. The lighter phase 9 is withdrawn as an overhead stream and the heavier phase 10 is withdrawn from the bottom of extractor 23.

The organic solvent should be substantially water-insoluble to minimize the amount of organic solvent dissolved in the aqueous fraction. Additionally, the solvent is preferably an azeotropic agent which serves to assist solvent recovery from the organic extract. Solvents which have proven to be particularly useful are C1 to C6 alkyl acetates, particularly n-propyl acetate (n-PA), isopropyl acetate, isobutyl acetate, sec-butyl acetate, ethyl acetate and n-butyl acetate, although other water-insoluble organic solvents having an appropriate density and a sufficiently low boiling point may also be used. N-propyl acetate and isopropyl acetate are particularly preferred due to their relatively low water solubility, excellent azeotropic behavior and their ability to remove the remaining acetic acid as well as high-boiling organic impurities from the aqueous mixture. Surprisingly, p-xylene, a conventional extraction solvent which is indigenous to the oxidation process, has been shown to be unsuccessful as a counter-current extraction solvent due to the large amounts of insoluble solids which accumulate in the extractor, precluding steady state operation.

The extraction can be effected using solvent ratios from about 1-4 parts solvent per part of extractor feed depending on the extractor feed composition. Space velocities of the combined feeds to the extractor generally range from 1 to about 3 $hr^{-1}$. Although the extraction can be done at ambient temperature and pressure, heating the solvent and extractor to about 30°-70° C., preferably 40°-60° C. is desirable. Although the lighter phase does contain very small amounts of the metal catalyst and corrosion metals, essentially all of the metal catalyst and the majority of the corrosion metals are contained in the heavier phase, stream 10.

The corrosion metals are removed by heating and filtering stream 10 in conventional means 25 to form stream 11 containing most of the catalyst and stream 12 containing most of the corrosion metals. The heat treatment is generally conducted for about 15 minutes to about 1 hour and at temperatures from about 70°-100° C., preferably 80°-100° C. Particularly preferred conditions are heating for about 95°-100° C. for about 30 minutes. During the heating the corrosion metal salts precipitate, provided the pH is in an acceptable range, typically greater than 3, preferably 4-6. By proper adjustment of the extract to feed ratio in the extractor, the pH of the heavier phase can be controlled so that the appropriate pH is attained and the corrosion metal salts are precipitated. Stream 10 can be filtered through conventional filters, to remove the corrosion metal salts. Typically, the corrosion metal salts can be sufficiently removed from the heavier phase via stream 12 to result in greater than 70% reduction of total corrosion metals. Stream 12 is then removed for disposal. Stream 11, which contains most of the metal catalyst, is active for the oxidation of p-xylene and can be recycled to the oxidation process, preferably after evaporative removal of residual extraction solvent and enough water to maintain the desired water concentration in the oxidation reactor.

The lighter phase, stream 9, which contains acetic acid, a minor amount of the water, the organic solvent, and the organic impurities may be distilled in conventional distillation apparatus 24 which can be a conventional column or a packed column. Recovered extraction solvent and acetic acid may be recycled to the extractor and oxidative reactor, respectively. The high-boiling organic impurities are removed as sludge from the base of the distillation column for disposal.

Obviously, numerous modifications and variations are possible in light of the above teachings. It is therefore to be understood that within the scope of the appended claims, the invention may be practiced otherwise than as specifically described herein.

We claim:

1. A method for removing impurities from an oxidative terephthalic acid synthesis mother liquor containing acetic acid, water, corrosion metals, a metal catalyst and organic impurities, comprising the steps of
   (a) concentrating the mother liquor by evaporating from 50-90% of the acetic acid and water contained therein,
   (b) adding an amount of water to the concentrated mother liquor sufficient to dissolve the metal catalyst and form an aqueous mixture,
   (c) extracting the aqueous mixture by counter-current extraction with a substantially water-insoluble organic solvent to produce a lighter phase containing the organic solvent, a minor amount of the water, acetic acid and the organic impurities and a heavier phase containing a major amount of the water, corrosion metals, and the metal catalyst, and
   (d) removing the corrosion metals from the heavier phase by heating and filtering, and
   (e) removing the organic impurities from the lighter phase by distillation.

2. The method of claim 1 wherein 80-90% of the acetic acid and water is removed in step (a).

3. The method of clam 1 wherein about 0.5-1.0 parts water is added per part of concentrated mother liquor in step (b).

4. The method of claim 3 wherein one part water per part concentrated mother liquor is added in step (b).

5. The method of claim 1 further comprising filtering the mother liquor prior to step (a) to remove isophthalic acid.

6. The method of claim 5 wherein the filtering is conducted at a temperature from about 20°-70° C.

7. The method of claim 1 further comprising heating the aqueous mixture to a temperature in the range from about 60°-95° C. for 0.5-4 hours prior to the extracting step to convert organic bromides present to inorganic bromides.

8. The method of claim 7 further comprising heating the aqueous mixture at a temperature in the range from about 80°-90° C. for 1-2 hours.

9. The method of claim 1 wherein step (c) is conducted at a temperature from 30°-70° C.

10. The method of claim 9 wherein step (e) is conducted at a temperature from about 40°-60° C.

11. The method of claim 1 wherein the heating and filtering in step (d) are conducted at a temperature in a range from 70°-100° C. for 15 minutes to 1 hour.

12. The method of claim 11 wherein the heating and filtering in step (d) are conducted at a temperature of about 95°-100° C. for about 30 minutes.

13. The method of claim 1 wherein about 1-4 parts of organic solvent per part of aqueous mixture are used in step (c).

14. The method of claim 1 wherein the organic solvent is isopropyl acetate or n-propyl acetate.

15. The method of claim 1 wherein the metal catalyst is a cobalt catalyst.

* * * * *

UNITED STATES PATENT AND TRADEMARK OFFICE
CERTIFICATE OF CORRECTION

PATENT NO. : 4,939,297

DATED : July 3, 1990

INVENTOR(S) : Larry W. Browder, James C. Medlin, and Art T. Spaugh, Jr.

It is certified that error appears in the above-identified patent and that said Letters Patent is hereby corrected as shown below:

Column 7, line 17, "90%" should be changed to ---95%---.

Signed and Sealed this

Tenth Day of September, 1991

Attest:

HARRY F. MANBECK, JR.

Attesting Officer

Commissioner of Patents and Trademarks